United States Patent [19]

Quinlan

[11] Patent Number: 4,543,358
[45] Date of Patent: Sep. 24, 1985

[54] ANTHELMINTIC GEL COMPOSITION AND A METHOD FOR THEIR PREPARATION AT AMBIENT TEMPERATURES

[75] Inventor: James M. Quinlan, Trenton, N.J.

[73] Assignee: American Cyanamid Company, Stamford, Conn.

[21] Appl. No.: 513,782

[22] Filed: Aug. 26, 1983

Related U.S. Application Data

[63] Continuation-in-part of Ser. No. 449,067, Dec. 13, 1982, abandoned.

[51] Int. Cl.$^4$ .......................................... A61K 31/425
[52] U.S. Cl. ................................................. 514/368
[58] Field of Search ........................ 424/270; 514/368

[56] References Cited

U.S. PATENT DOCUMENTS 4,287,176  9/1981  Demchak et al. .................. 424/170

Primary Examiner—Sam Rosen
Attorney, Agent, or Firm—H. G. Jackson

[57] ABSTRACT

This invention relates to aqueous gels, which remain gelatinous in a temperature range as low as −27° C. containing dl- or 1-6-phenyl-2,3,5,6-tetrahydro(—-)imidazo[2,1-b]thiazole, acylamino derivatives, thereof and pharmaceutically acceptable salts thereof, characterized by gelation and preparation at ambient temperatures (20°–60° C.), under vacuum, without additional heating or cooling in their preparation.

19 Claims, No Drawings

ANTHELMINTIC GEL COMPOSITION AND A METHOD FOR THEIR PREPARATION AT AMBIENT TEMPERATURES

This application is a continuation-in-part of application Ser. No. 449,067, filed Dec. 13, 1982, now abandoned.

SUMMARY OF THE INVENTION

The invention relates in particular to aqueous gels containing an anthelmintic compound of formula (I)

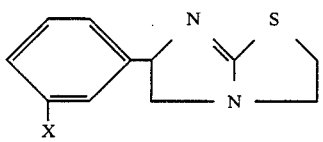

wherein X is hydrogen or —NHR; R is $C_2$–$C_5$ alkanoyl or benzoyl, and pharmaceutically acceptable salts thereof, characterized by preparation within the temperature range at which gelation occurs (20°–60° C.), under reduced pressure. Gels containing 15–50% gellant, water (15–50%), propylene glycol (14–31%), and an anthelmintic compound of formula I (3–25%) may conveniently be prepared by this method.

Among the compounds of formula (I) preferred are levamisole, tetramisole, butamisole or benzamisole.

The use of gels characterized by sub-zero gelation, as anthelmintic preparations is disclosed in U.S. Pat. No. 4,287,176 (1981). Specifically this patent discloses the use of anthelmintic gels and their formation at −23° to −20° C. The gellant used in these formulations is a nonionic surfactant of structure: α-hydro-Ω-hydroxy-poly(oxyethylene)poly(oxypropylene)poly(oxyethylene)block copolymer, average molecular weight 12,500; specific gravity 1.05; mp 56° C.; Brookfield viscosity 3100 at 77° C.; surface tension of a 0.1% aqueous solution: 40.6 dynes/cm at 25° C. (as measured on a die Nough tensiometer; U.S. Pat. No. 3,740,421 and others).

Recommended processes for preparing gels using this gellant are either a "cold" or "hot" technique in a temperature range where the gel is in a liquified state prior to gelation as described below and see Irving R. Schmolka, J. Biomed. MATER. RES., Vol. 6, pgs. 571–582 (1972).

The "cold" technique, is recommended as a first step to determine the feasibility of the potential gel system and to establish the optimum gellant concentration required. In this technique, the gellant is dissolved, along with the other ingredients, in water at a temperature of 5°–10° C. Aeration should be avoided. When solution is completed, usually after about two hours of stirring at 10° C., the system is allowed to warm up to room temperature, whereupon it forms a ringing gel. Water-insoluble ingredients may be dissolved in alcohol or acetone, cooled and added to the gellant solution. However, an alcohol content of 20% or greater should be avoided since these weaken the gel. Where alcohol cannot be tolerated, the water-insoluble materials should be heated with the gellant and cold water slowly added to the molten mixture to bring the temperature below that at which gelation occurs. This procedure has been used successfully with many water-insoluble organic compounds, including N,N-diethyltoluamide, amyl para-dimethylamino-benzoate and lauryl lactate.

The "hot" technique readily lends itself to production. In the laboratory, all ingredients are placed into a three-neck glass flask, equipped with a mechanical stirrer, reflux condenser and dropping funnel to prevent composition change due to loss of water. While dissolving the gellant, the mixture is heated to about 80° C., and stirred gently. Excessive agitation will cause the development of foam and should be avoided. When the system is homogeneous, transfer to containers. Upon cooling to room temperature, the product gels.

Unexpectedly we find that gels suitable but not limited to anthelmintic use may be prepared at ambient temperatures (20°–60° C.) under reduced pressure as demonstrated by the general procedure described below.

A gellant phase may be prepared by dissolving the gellant 15–50% and preferably 20–30% by weight of final formulation in propylene glycol 14–31% by weight at 60°–80° C. or alternatively, the gellant phase prepared completely at ambient temperatures as described below.

The gellant phase is prepared by slurrying the gellant 15–50% and preferably 15–35% by weight of formulation in propylene glycol 14–30% by weight for 15 minutes to one hour under reduced pressure 25–50 mm Hg at room temperature. The gellant selected is a nonionic surfactant of structure α-hydro-Ω-hydroxy-poly(oxyethylene)poly(oxypropylene)poly(oxyethylene) block copolymer, average molecular weight 12,500; mp 56° C.; Brookfield viscosity of 3100 at 77° C.; surface tension of a 0.1% aqueous solution: 40.6 dynes/cm (measured with a du Nouy tensiometer).

An aqueous solution containing the remaining ingredients may be prepared by dissolving a levamisole or tetramisole salt, preferably the hydrochloride, in amounts of from about 3% by weight to about 25% by weight and preferably 6–12% by weight of final formulation in deionized or distilled water used in amounts of from about 15% by weight to about 50% by weight and preferably 35–45% by weight of formulation. This solution is buffered by dissolving 1.5% by weight of citric acid and 1.0% by weight of trisodium citrate to provide a pH range at which long term chemical stability of the components is achieved, i.e. pH 3–3.5.

Optional components, which may be incorporated into the above solution at this stage are:

a. Benzyl alcohol added in amounts of from about 0.5% by weight to about 1.5% by weight and preferably 1.5% by weight of formulation, as an antimicrobial preservative;

b. the yellow dye C.I. Acid yellow No. 23; ("tartrazine"; F.D. & C yellow No. 5; 4,5-dihydro-5-oxo-1-(4-sulfophenyl)-4-[(sulfophenyl)azo]-1H-pyrazole-3-carboxylic acid trisodium salt) used as coloring agent in amounts of from about 0.01% by weight to about 0.03% by weight and preferably 0.01% by weight of formulation;

c. an antifoaming agent comprising a mixture of dimethylpolysiloxanes of structure:

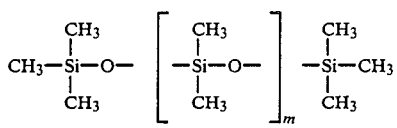

and silica gel, wherein the calculated average value of m is 200–350, the mixture is a water-white viscous oil-like liquid; d=0.965–0.970; $n_D{}^{25}$ about 1.404; viscosity about 60,000 centistrokes (and said antifoaming agent is described in U.S. Pat. No. 2,441,098) used in amounts of from 0.001–0.02% by weight and preferably 0.02% by weight of formulation.

The anthelmintic gel is prepared by simply mixing either of the above gellant phases and the aqueous solution from one-half to two hours under reduced pressure of from 10–100 mm Hg and preferably 25–50 mm Hg at ambient temperatures of from 20°–60° C., without the requirements of either additional heating or cooling. This procedure gives an air free gel which is suitable for administering exact dosages of anthelmintic by volume. When careful control of dosage of active ingredients to be administered by volume is not necessary and when the presence of air in the gel is acceptable in the final formulation, the preparation may be carried out at pressures up to and including atmospheric pressure.

By the above method a typical gel of the invention may be prepared by dissolving 11.6 g of levamisole or tetramisole hydrochloride, 1.5 g citric acid monohydrate, 1.0 g sodium citrate dihydrate, 1.5 g of benzyl alcohol and 0.01 g of the yellow dye C.I. Acid yellow No. 23 in 39 g of water. Next, a solution of the above gellant 26 g in propyleneglycol 19.39 g is prepared by mixing at 60° C. Then the solutions are mixed together under a 25–50 mm Hg until a homogeneous mixture is obtained at 20°–60° C. without additional heating or cooling. The gel formed has a gelation temperature range of from −15° to −18° C.; viscosity of the gel is $0.51 \times 10^{+6}$; and the water gellant ratio is 1.5/1.0.

The above procedure is equally suitable to prepare gels of the inventions containing but not limited to other anthelmintic compounds defined and described by formula (I) above.

This procedure for preparing these aqueous gels offers several advantages over existing methods. Cold techniques often limit the concentration range of ingredients due to increasing viscosities and decreases in solubility of the components as the temperature of gelation is lowered; this would be particularly true when operating temperatures approaching the freezing point of the mixture are required. By the ambient temperature method of the present invention, gels with sub-zero gelation points containing 20 to 30% gellant with water to gellant ratios of 0.54/1 to 1.4/1 may be prepared. This is a distinct advantage over prior methods of preparing gels with sub-zero gelation points since clear homogenous gels with water to gellant ratios as low as 1/4/1 containing 20 to 30% by weight of the gellant are difficult to prepare, frequently requiring more than 36 hours at temperatures below the gelation point to obtain complete solution. Thus, the method of the present invention provides for the preparation of gel compositions with sub-zero gelation points which are not obtainable by prior methods available in the art. Gel compositions with sub-zero gelation points containing 15 to 50% by weight of the gellant and water to gellant ratios of 0.54/1 to 1.4/1 are now readily obtainable. Additionally, processing at temperatures below ambient often require the use of specialized cooling systems which are more expensive and difficult to maintain and operate.

Chemical thermal instability of one or more of the components often limit the use of a hot technique particularly since gellants of this type are less soluble at elevated temperatures, adding to processing times at higher temperatures.

An additional advantage of these gels and their method of preparation at ambient temperatures (20°–60° C.) is that they may also be fortified if necessary at ambient temperatures. Frequently in the manufacture of products it is necessary to adjust the concentration of the components to be within finite limits; this would be particularly true in food related and pharmaceutical products. The aqueous gels of this invention may conveniently be fortified by simple addition of the required ingredient, either as a solid or as an aqueous solution, followed by mixing under reduced pressure until a homogeneous mixture is obtained without being liquified.

The above stated advantageous features of said aqueous gels make them eminently suitable for use as carriers for active ingredients which is meant to include the biologically active component and desired additives including coloring agents, flavoring agents, conditioners, etc., as indicated by the following nonlimiting examples.

Cosmetics, hair preparations, dental products, veterinary products such as anthelmintics, pharmaceutical products administered as gels, pesticide products such as insecticides, herbicides, etc., could conviently be incorporated and applied in said aqueous gels. Further, the method of preparation of these gels readily lends itself to any method of production, batch, semi-batch or continuous processing, which enhances their attractiveness for use in the above areas.

EXAMPLE 1

Preparation of levamisole gels

General Procedure

The appropriate amounts of levamisole salt as the hydrochloride, citric acid monohydrate, trisodium citrabe, benzyl alcohol, yellow dye (C.I. Acid yellow No. 23) are dissolved in deionized or distilled water and the solution clarified if necessary. Next, a homogeneous gellant solution containing the appropriate amount of gellant and propylene glycol is prepared by mixing at 60°–80° C. The gellant selected is a nonionic surfactant of structure: α-hydro-Ω-hydroxy-poly(oxyethylene)-poly(oxypropylene)poly(oxyethylene) block copolymer, average molecular weight 12,500; mp 56° C.; Brookfield viscosity of 3100 at 77° C.; surface tension of a 0.1% aqueous solution: 40.6 dynes/cm (measured with a du Nouy tensiometer). Then the two solutions are mixed together at ambient temperatures (20°–60° C.) under reduced pressure 25–50 mm Hg until a homogeneous mixture is obtained.

The composition of the formulations and other data obtained are summarized in Table I below.

TABLE I

| Composition and physical parameters of various levamisole gels | | | | | | | | | | | |
|---|---|---|---|---|---|---|---|---|---|---|---|
| | Percent by weight Composition of formulations | | | | | | | | | | |
| Component | No. 1 | No. 2 | No. 3 | No. 4 | No. 5 | No. 6 | No. 7 | No. 8 | No. 9 | No. 10 | No. 11 |
| Levamisole HCl | 10.49 | 12.00 | 11.60 | 11.60 | 11.60 | 11.73 | 11.71 | 11.71 | 11.73 | 11.73 | 23.46 |
| Water | 50.00 | 45.00 | 45.00 | 40.00 | 39.00 | 37.50 | 28.26 | 18.86 | 34.50 | 40.31 | 30.50 |
| Gellant | 20.00 | 20.00 | 25.00 | 25.00 | 26.00 | 25.00 | 30.00 | 35.00 | 28.00 | 29.00 | 28.00 |
| Citric Acid Monohydrate | 1.50 | 1.50 | 1.50 | 1.50 | 1.50 | 1.50 | 1.50 | 1.50 | 1.50 | 1.50 | 1.50 |
| Trisodium citrate, dihydrate | 1.00 | 1.00 | 1.00 | 1.00 | 1.00 | 1.00 | 1.00 | 1.00 | 1.00 | 1.00 | 1.00 |
| Benzyl alcohol | — | — | 1.50 | 1.50 | 1.50 | 1.50 | 1.50 | 1.50 | 1.50 | 1.50 | 1.50 |
| C.I. Acid yellow No. 23 | 0.01 | 0.01 | 0.01 | 0.01 | 0.01 | 0.01 | 0.01 | 0.01 | 0.01 | 0.01 | 0.01 |
| Antifoaming Agent | — | — | — | — | — | 0.02 | 0.02 | 0.02 | 0.02 | 0.02 | 0.02 |
| Propylene glycol | 17.00 | 20.04 | 14.39 | 19.39 | 19.39 | 21.74 | 26.00 | 30.40 | 21.74 | 14.93 | 14.01 |
| Total | 100.00 | 100.00 | 100.00 | 100.00 | 100.00 | 100.00 | 100.00 | 100.00 | 100.00 | 100.00 | 100.00 |
| Water gellant Ratio | 2.5/1.0 | 2.25/1.0 | 1.8/1.0 | 1.6/1.0 | 1.5/1.0 | 1.5/1.0 | 0.94/1 | 0.54/1 | 1.23/1 | 1.39/1 | 1.09/1 |
| Gelation temperature °C. | +11 to +13 | +6 to +10 | −7 to −9 | −11 to −14 | −15 to −18 | −15 to −18 | <−27 | <−27 | −25 | — | — |

EXAMPLE 2

Fortification of subpotent levamisole gels

General Procedures

Following the procedure of Example 1, the appropriate amounts of levamisole hydrochloride, citric acid, trisodium citrate, benzyl alcohol and yellow dye (C.I. Acid yellow No. 23) are dissolved in deionized water. Following the same procedure, the appropriate amounts of citric acid, trisodium citrate, benzyl alcohol and yellow dye (C.I. Acid Yellow No. 23) are dissolved in deionized water. These two aqueous solutions are combined in the proper proportions to give the desired amount of solution containing 80% of the desired levamisole hydrochloride. Next, a homogeneous gellant solution containing the appropriate amounts gellant as defined in Example 1 and propylene glycol is prepared by mixing at 60°–80° C.

The above gellant and aqueous solutions are then mixed together at ambient temperatures (20°–60° C.) under reduced pressure (25–50 mm Hg) for one hour. A sample is withdrawn for analysis. Sample 1.

A 50.40% w/w levamisole hydrochloride aqueous solution was added to bring the levamisole hydrochloride content from 80–90% of the required amount and the mixture stirred for one hour at ambient temperatures without additional heating or cooling, under reduced pressure (25–50 mm Hg). A sample is taken for analysis. Sample 2.

Solid technical levamisole hydrochloride is then added to bring the potency to 100% of the required amount and the mixture stirred at ambient temperature without additional heating or cooling for one hour under reduced pressure (25–50 mm Hg). A sample is taken for analysis. Sample 3.

The results of the fortificatons of the formulations and other data are summarized in Table II below.

TABLE II

| Fortification of levamisole hydrochloride gel from 9.74 to 12.27% | | | |
|---|---|---|---|
| | Sample 1 | added as aqueous solution | Sample 3 added as solid |
| Theorectical % levamisole hydrochloride w/w | 9.43 | 10.72 | 12.20 |
| Assay % w/w levamisole hydrochloride | 9.74 | 10.63 | 12.27 |
| Gel point of resulting gel | −19 to −20° C. | −17 to −18° C. | −18 to −19° C. |
| Viscosity of resulting gel (Brookfield RVT-RL-345, T.E. spindle at 0.5 rpm) | $3.24 \times 10^{+6}$ cps | $3.10 \times 10^{+6}$ cps | $3.02 \times 10^{+6}$ cps |

EXAMPLE III

Preparation of aqueous gels at ambient temperatures

The appropriate amounts of gellant as defined in Example I, either as a homogeneous solution at 60°–80° C., or as a slurry prepared by stirring under reduced pressure 25–50 mm Hg for 15 minutes to one hour at room temperature, in propylene glycol is added to the desired amount of water at ambient temperature. The resulting mixture is then stirred under reduced pressure of 25–50 mm Hg at ambient temperature 20°–60° C. until a homogeneous mixture is obtained. The composition and viscosity data of aqueous gels prepared by this procedure are included in Table III.

TABLE III

| Clear aqueous gels | | | |
|---|---|---|---|
| Component | Percent by weight composition | | |
| Gellant (slurry or solution) | 35.00 (solution) | 35.00 (slurry) | 40.00 (slurry) |
| Propylene glycol | 30.44 | 30.44 | 30.00 |
| Water | 34.56 | 34.56 | 30.00 |
| Total | 100.00 | 100.00 | 100.00 |
| Water gellant ratio | 0.987/1 | 0.987/1 | 0.75/1 |
| Viscosity of gel (Brookfield T.E. spindle at 0.5 rpm) Model RVT | $5.6 \times 10^6$ | $5.6 \times 10^6$ | $7.2 \times 10^6$ |

We claim:

1. A method for the preparation, at ambient temperatures, of clear aqueous homogeneous gels characterized by subzero gelation points, comprising, mixing about 15–50% by weight of the gellant α-hydro-Ω-hydroxy-poly(oxyethylene)poly(oxypropylene)poly(oxyethylene) block copolymer, average molecular weight 12,500; mp 56° C., Brookfield viscosity of 3100 at 77° C.; surface tension of a 0.1% aqueous solution: 40.6 dynes/cm (measured with a du Nouy tensiometer) with 14–31% by weight of propylene glycol, 0–41% by weight of one or more active ingredients, and admixing the thus formed mixture with about 30–50% by weight of water and stirring the resulting mixture at ambient temperatures (20°–60° C.) without additional heating or cooling, until it is homogeneous at atmospheric pressure or under reduced pressure of from 10–100 mm Hg.

2. A method according to claim 1 in which the gellant is present in 20–30% by weight.

3. A method according to claim 1 wherein the reduced pressure is 25–50 mm Hg.

4. A method according to claim 1 wherein the aqueous gel is prepared at atmospheric pressure.

5. A method according to claim 1 in which the gellant is dissolved in the propylene glycol at 60°–80° C.

6. A method according to claim 1 wherein the gellant is a slurry in propylene glycol (20°–60° C.).

7. A method according to claim 1 wherein the active ingredient is dissolved in the water phase.

8. A method according to claim 1 wherein the active ingredient is dissolved in the propylene glycol phase.

9. A method according to claim 1 wherein the active ingredients are dissolved in both the aqueous and propylene glycol phases.

10. A aqueous composition comprising: 3–25% by weight of a pharmaceutically acceptable salt of the anthelmintic compound of the formula:

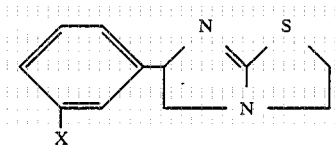

wherein X is hydrogen or —NH—R; R is $C_2$–$C_5$ alkanoyl or benzoyl; or the optical isomers thereof; 30–50% by weight of water; 14–31% by weight of propylene glycol; and greater than 30% by weight of the gellant α-hydro-Ω-hydroxy-poly(oxyethylene)poly(oxypropylene)poly(oxyethylene) block copolymer, average molecular weight 12,500, specific gravity 1.05; mp 56° C., viscosity 3100 at 77° C.; wherein said compositions are gels in the temperature range of from −20° to +60° C.; with the proviso that the water/gellant ratio is from 0.54/1.0 to 2.0/1.0; and that the components of said composition add up to a total of 100% by weight.

11. An aqueous gel composition according to claim 10 comprising: 3–25% by weight of a pharmaceutically acceptable salt of the anthelmintic 1-6-phenyl-2,3,5,6-tetrahydroimidazo[2.1-b]thiazole or dl-6-phenyl-2,3,5,6-tetrahydroimidazo[2,1-b]-thiazole; 14–31% by weight of propylene glycol; an antimicrobially effective amount of benzyl alcohol; at least 15% by weight of water; about 1.5% by weight of citric acid; about 1.0% by weight of trisodium citrate acid; at least greater than 30% by weight of the gellant α-hydro-Ω-hydroxy-poly(oxyethylene)poly(oxypropylene)poly(oxy-ethylene) block copolymer which has an average molecular weight of 12,500 and a specific gravity of 1.05 and provided that the ratio of water to gellant is in the range of from 0.54/1.0 to 1.66/1 and a sufficient amount of a buffer to adjust the pH of the finished gel composition to between pH 3.0 and 3.5.

12. A composition according to claim 11, wherein the anthelmintic is 1-6-phenyl-2,3,5,6-tetrahydroimidazo[2,1-b]thiazole.

13. A composition according to claim 11 comprising 6–12% by weight of said anthelmintic; 35–45% by weight of water; 1.5% by weight of citric acid; 1.0% by weight of trisodium citrate; 14–31% by weight of propylene glycol; greater than 30% by weight of said gellant; 0.5–1.5% by weight of benzyl alcohol; 0.01–0.03% by weight of C.I. Acid yellow No. 23; 0.001–0.02% by weight of an antifoaming agent comprising a mixture of dimethylpolysiloxanes of formula:

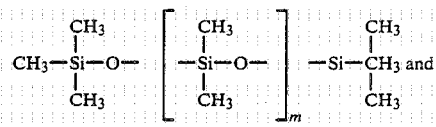

silica gel wherein the calculated average value of m is 200–350, the mixture is a viscous liquid, d=0.965–0.970, $n_D^{25}$ about 1.404, viscosity about 60,000 centistokes; with the proviso that the water/gellant ratio is from 1.5/1.0 to 2.0/1.0.

14. A composition according to claim 13 comprising: 11.73% by weight of the hydrochloride of said anthelmintic; 37.5% by weight of water; 1.5% by weight of citric acid; 1.0% by weight of trisodium citrate; 21.74% by weight of propylene glycol; greater than 30% by weight of said gellant; 1.5% by weight of benzyl alcohol; 0.01% by weight of C.I. Acid yellow No. 23 and 0.02% by weight of said antifoaming agent.

15. A method for the preparation of an aqueous composition, comprising; dissolving 3–25% by weight of a pharmaceutically acceptable salt of the anthelmintic compound of formula:

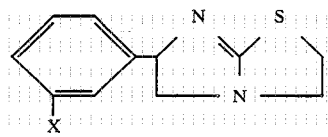

wherein X is hydrogen or —NH—R; R is $C_2$–$C_5$ alkanoyl or benzoyl; or the optical isomers thereof; 1.5% by weight of citric acid and 1.0% by weight of trisodium citrate; 0.5% by weight of benzyl alcohol; 0.01–0.03% by weight of C.I. Acid yellow No. 5; 0.001–0.02% by weight of an antifoaming agent comprising a mixture of dimethylpolysiloxanes of formula:

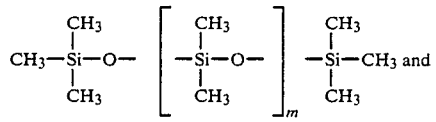

silica gel wherein the calculated average value of m is 200–350, the mixture is a viscous liquid, d=0.965–0.970, $n_D^{25}$ about 1.404, viscosity about 60,000 centistokes, in 15–50% by weight of water and preferably 20–30% by weight of the gellant α-hydro-Ω-hydroxy-poly(oxyethylene)poly(oxypropylene)poly(oxyethylene) block copolymer, average molecular weight 12,500; specific gravity 1.05; mp 56° C.; viscosity 3100 at 77° C. dissolved or slurried in 14–31% by weight of propylene glycol at from 60°–80° C.; and stirring said mixture at ambient temperatures of from 20°–60° C., under reduced pressure of from 25–50 mm Hg until a clear solution occurs; with the provisos that the water/gellant ratio is from 0.94/1.0 to 2.5/1 and that the components of said composition add up to a total of 100%.

16. A method according to claim 15 wherein the anthelmintic is 1-6-phenyl-2,3,5,6-tetraimidazo[2,1-b]-thiazole, or dl-6-phenyl-2,3,5,6-tetrahydroimidazo[2,1-b]-thiazole, or a pharmaceutically acceptable salt thereof.

17. An aqueous composition comprising: 3-25% by weight of a pharmaceutically acceptable salt of the anthelmintic compound of the formula:

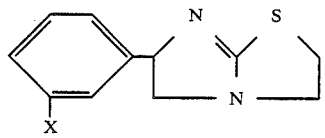

wherein X is hydrogen or —NH—R; R is $C_2$-$C_5$ alkanoyl or benzoyl; or the optical isomers thereof; 30-50% by weight of water; 14-31% by weight of propylene glycol; and 15-30% by weight of the gellant α-hydro-Ω-hydroxy-poly(oxyethylene)poly(oxypropylene)-poly(oxyethylene) block copolymer, average molecular weight 12,500, specific gravity 1.05; mp 56° C., viscosity 3100 at 77° C.; wherein the compositions are gels in the temperature range of from −20° to +60° C.; with the proviso that the water/gellant ratio is from 0.54/1.0 to 1.39/1.0; and that the components of the composition add up to a total of 100% by weight.

18. An aqueous gel composition according to claim 17 comprising; 3-25% by weight of a pharmaceutically acceptable salt of the anthelmintic 1-6-phenyl-2,3,5,6-tetrahydroimidazo[2,1-b]thiazole or dl-6-phenyl-2,3,5,6-tetrahydroimidazo[2,1-b]thiazole; 14-31% by weight of propylene glycol; an antimicrobially effective amount of benzyl alcohol; at least 15% by weight of water; about 1.5% by weight of citric acid; about 1.0% by weight of trisodium citrate acid; 20-30% by weight of the gellant α-hydro-Ω-hydroxy-poly(oxyethylene)-poly(oxypropylene)poly(oxyethylene) block copolymer which has an average molecular weight of 12,500 and a specific gravity of 1.05 and provided that the ratio of water to gellant is in the range of from 0.54/1.0 to 1.39/1 and a sufficient amount of a buffer to adjust the pH of the finished gel composition to between pH 3.0 and 3.5.

19. A composition according to claim 18 wherein the anthelmintic is 1-6-phenyl-2,3,5,6-tetrahydroimidazo[2,1-b]thiazole.

* * * * *